United States Patent [19]

Hünnebeck

[11] Patent Number: 5,111,536
[45] Date of Patent: May 12, 1992

[54] EYEGLASSES PROTECTIVE AGAINST GASES

[75] Inventor: Volker Hünnebeck, Berlin, Fed. Rep. of Germany

[73] Assignee: Auergesellschaft GmbH, Fed. Rep. of Germany

[21] Appl. No.: 276,217

[22] Filed: Nov. 23, 1988

[30] Foreign Application Priority Data

Mar. 12, 1988 [DE] Fed. Rep. of Germany ....... 3740949

[51] Int. Cl.$^5$ ................................................ A61F 9/02
[52] U.S. Cl. ........................................... 2/428; 2/439
[58] Field of Search ................... 2/440, 441, 439, 454, 2/426, 428, 429, 430, 431, 436, 437, 432, 452; 351/43

[56] References Cited

U.S. PATENT DOCUMENTS

| Re. 12,816 | 6/1908 | Cover | 2/440 |
| 1,949,595 | 3/1934 | Willson et al. | 2/441 X |
| 2,321,159 | 6/1943 | Ryan | 2/441 |
| 4,698,857 | 10/1987 | Kastendieck et al. | 2/428 X |

FOREIGN PATENT DOCUMENTS

| 0457339 | 6/1949 | Canada | 2/436 |
| 0421744 | 1/1911 | France | 2/436 |

Primary Examiner—Peter Nerbun
Attorney, Agent, or Firm—Reed Smith Shaw & McClay

[57] ABSTRACT

The present invention pertains to safety eyeglasses. The safety eyeglasses protect a user against gases. The eyeglasses include a frame having a flat surface and an eye space surrounding both eyes of a user. The eye space is equipped with fittings to accept eye lenses. These fittings are attached asymmetrically at the corresponding angle (60) to the flat surface. The improvement in the safety eyeglasses comprises, on the flat surface of the eye glass frame protruding from this surface, a first and second single fold bellow forming a first and second eye space, respectively, and fittings for the eyeglasses which are a part of the bellow.

6 Claims, 1 Drawing Sheet

EYEGLASSES PROTECTIVE AGAINST GASES

FIELD OF THE INVENTION

The present invention concerns safety glasses comprising an eyeglass frame and eye spaces surrounding both eyes of the user, with fittings to accept permanently inserted eye lenses.

BACKGROUND OF THE INVENTION

In the case of known safety glasses of this type, the eyeglass frame, typically consisting of a flexible material, is arched in the area of the eyes and of the forehead according to the shape of the head. In the area of the eyes this arched design forms an eye space which is equipped with a fitting to accept the eye lenses. In this case, the fitting consists of a metal ring element inserted into the eye space with which one side is in contact with the eye lens, pressing it against a convex rim in the eye space. In order to provide a firm connection and the necessary sealing between the eye lens and the eye space, a tension clamp is installed over the ring element. This safety glass design has disadvantages since the use of a metal ring element with a tension clamp increases the weight of the safety glasses, and since the design of the safety glasses is generally too rigid, with the result that the safety glasses in a packaged condition requires relatively much space.

It is therefore the task of the invention to design safety glasses of the above-mentioned type which can be folded together closely, allowing a user to press together the eyeglass frame and the fittings with the eye lenses into a flat package, and in addition to have eyeglasses having low weight.

According to the invention, this problem is solved with a design where, on the flat surface of the eyeglass frame and at a distance from this surface, there are two bellows, each designed as an eye space, and being asymmetrically attached thereto, and where the fittings for the eye lenses are designed as part of the bellow.

According to a further version of the invention, the eyeglass frame with the bellows and the fitting for the eye lenses is designed as one unit, consisting of an elastic plastic material with high resilience. This makes it possible to insert the eye lenses under a certain prestress force tightly into the fittings eliminating otherwise necessary tension clamps and similar devices. Another advantage can be seen in the fact that the bellow forms some kind of buffer zone between the dimensionally stable fitting for the eye lenses and the eyeglass frame which adapts to the face, which means that when the eyeglass frame is placed on the face, the eye lenses will remain fixed in the fitting without the need to place a tension clamp around the fitting.

SUMMARY OF THE INVENTION

The present invention pertains to safety eyeglasses. The safety eyeglasses protect a user against gases. The eyeglasses include a frame having a flat surface and an eye space surrounding both eyes of a user. The eye space is equipped with fittings to accept eye lenses. These fittings are attached asymmetrically at the corresponding angle ($\alpha$) to the flat surface. The improvement in the safety eyeglasses comprises on the flat surface of the eye glass frame protruding from this surface, a first and second single fold bellow forming a first and second eye space, respectively, and fittings for the eyeglasses which are a part of the bellow.

Other details, objects and advantages of the invention will become apparent as the following description of the presently preferred embodiments and presently preferred methods of practicing the invention proceeds.

BRIEF DESCRIPTION OF THE DRAWINGS

In the accompanying drawings, the preferred embodiments of the invention and preferred methods of practicing the invention are illustrated in which.

DESCRIPTION OF THE PREFERRED EMBODIMENT

Figure 1:
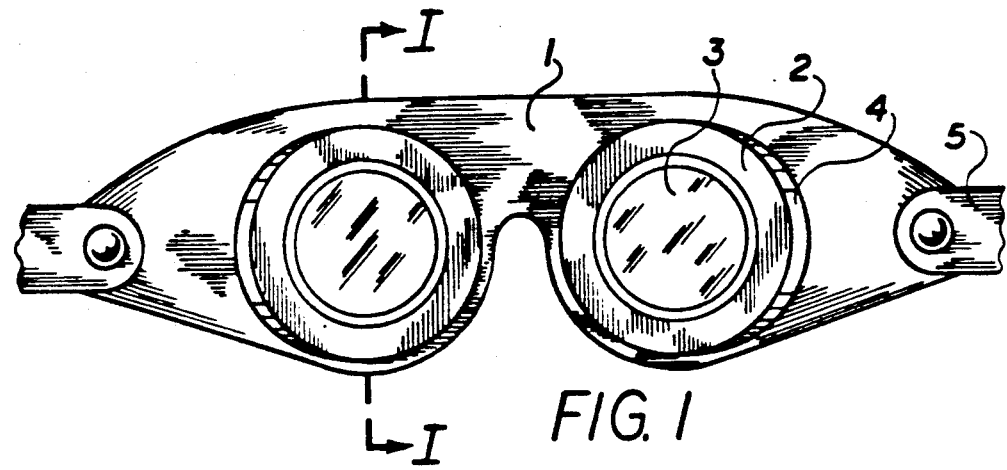
FIG. 1 is a front view of the safety glasses according to the invention.
Figure 2:
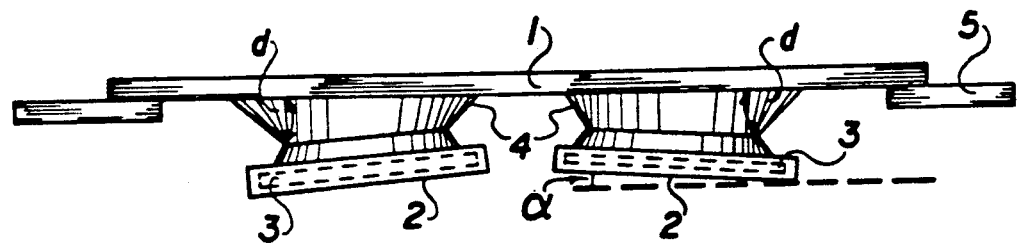
FIG. 2 is a top view of the safety glasses.

As shown in FIGS. 1 and 2, the safety glasses are comprised of an eyeglass frame 1, on which there are two bellows 4, each of which are protruding from the flat surface of the eyeglass frame 1 and which are attached asymmetrically. The safety glasses are also comprised of a fitting 2 provided on each bellow 4, into which an eye lens 3 is captively and tightly inserted.

Figure 3:
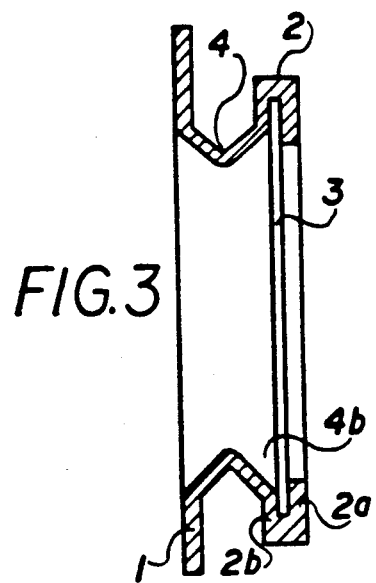
FIG. 3 is an enlarged sectional representation along the line I—I in FIG. 1.

FIG. 3 shows that the fitting 2 is designed as a frame which surrounds the eye lens 3 at its circumference, and that this frame has a front fitting rim 2a and a rear fitting rim 2b. The fitting rims 2a and 2b exert on both sides of the eye lens 3 inserted into the fitting 2 so much prestress force that the eye lenses are surrounded by the fitting frame captively and gas tight. The eyeglass frame 1 with the bellows 4 and with the fittings 2 is made from elastic plastic material, preferably from silicon elastomer material with high resilience. The elastic eyeglass frame 1 adapts to different facial shapes.

Figure 4:
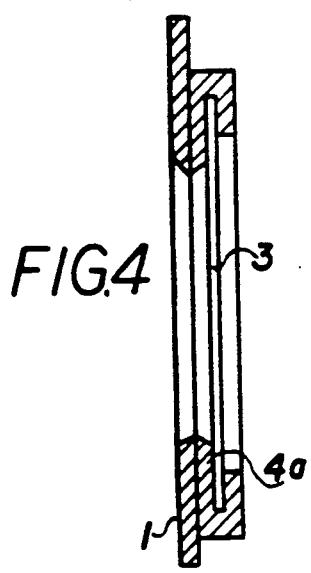
FIG. 4 is a sectional representation according to FIG. 3, where the fitting with the eye lenses, via the bellow according to the invention are pressed closely against the eyeglass frame.

FIG. 4 shows how the bellow 4 is folded flat together with the eye lens 3 of the eye space, in such a way that one bellow part 4a of the bellow 4 is in contact with the eye lens 3 with a large surface, thus protecting the eye lens from being pushed out towards the inside.

In view of the fact that the eye space is designed as an elastic bellow, the bellow pocket 4b facing the eye lens 3 offers the advantage of serving as a space for the collection of perspiration and/or condensation water, preventing this from coming in contact with the skin of the user.

In the operation of the preferred embodiment, the bellows 4 are extended from the flat surface of the eyeglass frame 1. The eyeglass frame 1 is placed over the eyes of a user and held on the user's head with a strap 5. As the strap 5 and frame 1 are fitted on the head of the user, due to the curvature of the face, the lenses 3 that are at rest at an angle $\alpha$ with the flat surface of the frame 1 become positioned essentially in parallel with the user's eyes so any distortion is completely or almost completely removed.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. Safety eyeglasses which protect against gases, wherein the eyeglasses include a frame, made from a pliable material, having a flat surface and eye openings surrounding both eyes of a user, the area around said eye openings equipped with fittings to accept eye lenses, with said fittings attached asymmetrically at a corresponding angle ($\alpha$) to the flat surface, the improvement comprising:

on the flat surface of the eyeglass frame and protruding from the surface, first and second single-fold bellows surrounding the first and second eye openings, which allows the bellows to fold together flat, and the fittings for the eye lenses being attached to the bellows.

2. Safety eyeglasses according to claim 1, wherein the eyeglass frame and the single-fold bellows with the fitting for the eye lenses are designed as one unit comprised of an elastic plastic material with high resilience.

3. Safety eyeglasses according to claims 1 or 2, wherein the plastic material of the safety glasses is a silicon elastomer.

4. Safety eyeglasses according to claim 3, wherein the fittings are each designed as a frame surrounding the eye lenses on both sides, and that this frame has a front and rear fitting rim.

5. Safety eyeglasses according to claim 4, wherein the fitting rims exert a prestress force on both sides of the eye lenses such that the eye lenses are held captive and gastight in the fittings.

6. Safety eyeglasses according to claim 1, wherein the single-fold bellows which can be folded together flat with the eye lenses then has one folded part of the bellows which has a large surface area in contact with the eye lens, thus preventing the eye lens from being pushed out towards the inside.

* * * * *